(12) United States Patent
Namba et al.

(10) Patent No.: US 9,877,927 B2
(45) Date of Patent: Jan. 30, 2018

(54) INHIBITOR OF ODOR CAUSED BY FURANEOL

(71) Applicant: Kao Corporation, Chou-ku, Tokyo (JP)

(72) Inventors: Aya Namba, Katsushika-ku (JP);
Naoko Saito, Utsunomiya (JP);
Michiaki Inoue, Cincinnati, OH (US);
Tsuyoshi Toyabe, Funabashi (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/519,962

(22) Filed: Oct. 21, 2014

(65) Prior Publication Data

US 2015/0110731 A1 Apr. 23, 2015

(30) Foreign Application Priority Data

Oct. 22, 2013 (JP) ................. 2013-219337

(51) Int. Cl.
| | |
|---|---|
| *A61K 36/53* | (2006.01) |
| *A61K 36/752* | (2006.01) |
| *A61K 31/05* | (2006.01) |
| *A61K 31/11* | (2006.01) |
| *A61K 31/12* | (2006.01) |
| *A61K 31/045* | (2006.01) |
| *A61K 31/122* | (2006.01) |
| *A61K 31/10* | (2006.01) |
| *A61K 31/19* | (2006.01) |
| *A61K 36/00* | (2006.01) |

(52) U.S. Cl.
CPC ............ *A61K 31/045* (2013.01); *A61K 31/05* (2013.01); *A61K 31/11* (2013.01); *A61K 31/12* (2013.01); *A61K 31/122* (2013.01); *A61K 31/19* (2013.01); *A61K 36/00* (2013.01)

(58) Field of Classification Search
None
See application file for complete search history.

(56) References Cited

U.S. PATENT DOCUMENTS

| 5,480,674 | A | * | 1/1996 | Peterson | ............... A23L 2/56 |
| | | | | | 426/534 |
| 7,074,419 | B2 | | 7/2006 | Dietz et al. | |
| 7,846,890 | B2 | * | 12/2010 | Vial | ............... C07D 317/70 |
| | | | | | 512/1 |
| 2006/0165622 | A1 | * | 7/2006 | Hiramoto | ............ A61K 8/347 |
| | | | | | 424/65 |
| 2007/0041917 | A1 | * | 2/2007 | Thomas | ............ A61Q 19/04 |
| | | | | | 424/59 |
| 2007/0071780 | A1 | * | 3/2007 | Dubois | ................ A61K 8/11 |
| | | | | | 424/401 |
| 2010/0248962 | A1 | * | 9/2010 | Wilczynski | ........... A01N 39/04 |
| | | | | | 504/101 |
| 2011/0274643 | A1 | * | 11/2011 | Yontz | .................. A61K 8/25 |
| | | | | | 424/76.1 |
| 2013/0210775 | A1 | | 8/2013 | Kato et al. | |
| 2015/0110669 | A1 | | 4/2015 | Namba et al. | |
| 2015/0111229 | A1 | | 4/2015 | Namba et al. | |

FOREIGN PATENT DOCUMENTS

| JP | 2001-247452 A | 9/2001 |
| JP | 2004-167218 A | 6/2004 |
| JP | 4579509 B | 9/2010 |
| JP | 2011-105690 A | 6/2011 |
| JP | 2012-250958 A | 12/2012 |
| JP | 2013-147475 A | 8/2013 |
| JP | 2015-081237 A | 4/2015 |
| WO | WO 2009/078360 A1 | 6/2009 |

OTHER PUBLICATIONS

Fact Sheet for Oxacyclohexadecen-2-one (downloaded Dec. 8, 2016, from https://us.lgcstandards.com/CA/en/Oxacychlohexadecen-2-one-Globalide-/p/DRE-C15757500).*
Product information sheet on Lemon Oil published online by the Sigma Aldrich Chemical Company (downloaded Dec. 8, 2016 from http://www.sigmaaldrich.com/catalog/product/saj/230380?lang=en&region=US).*
Indo, M., Synthetic Flavor and Fragrance, Enlarged and Revised Edition, 2005, The Chemical Daily Co., Ltd., Tokyo, Japan, pp. 348-349.
Cutzach, I et al., "Identification of volatile compounds with a 'toasty' aroma in heated oak used in barrelmaking," J Agric Food Chem, Jun. 1997, 45: 2217-2224, Am. Chem Soc, Washington, DC.
Karagül-Yüceer, Y et al., "Aroma characterization of fresh and stored—nonfat dry milk," Chapter 8 in Freshness and Shelf Life of Foods, ACS Symposium Series vol. 836, Keith R. Cadwallader et al., eds., Oct. 2002, pp. 108-123, Am. Chem. Soc, Washington, DC.
Botelho, G et al., "Characterisation of free and glycosidically bound odourant compounds of Aragonez clonal musts by GC-O," Anal Chim Acta, Jan. 2010; 657(2): 198-203, Elsevier, Amsterdam, Netherlands.
Excerpted file history, U.S. Appl. No. 14/519,958, filed Oct. 21, 2014, downloaded from the U.S. Patent and Trademark Office, Alexandria, VA: (issue notification dated Feb. 10, 2016; Notice of allowance dated Dec. 11, 2015; Amendment and reply filed Nov. 25, 2015 and Office action dated Aug. 28, 2015).

* cited by examiner

*Primary Examiner* — Frederick Krass
*Assistant Examiner* — Michael P Cohen
(74) *Attorney, Agent, or Firm* — Sterne, Kessler, Goldstein & Fox, P.L.L.C.

(57) ABSTRACT

Provided is a substance inhibiting an odor caused by 2,5-dimethyl-4-hydroxy-3(2H)-furanone. An inhibitor of an odor caused by 2,5-dimethyl-4-hydroxy-3(2H)-furanone, comprising a substance inhibiting the response of an olfactory receptor OR5K1 as an active ingredient.

18 Claims, 2 Drawing Sheets

```
                        SEQUENCE LISTING

<160> NUMBER OF SEQ ID NOS: 2

<210> SEQ ID NO 1
<211> LENGTH: 927
<212> TYPE: DNA
<213> ORGANISM: Homo sapiens
<220> FEATURE:
<223> OTHER INFORMATION: DNA encoding human OR5K1

<400> SEQUENCE: 1
atggctgaag aaaatcatac catgaaaaat gagtttatcc tcacaggatt tacagatcac      60
cctgagctga agactctgct gtttgtggtg ttctttgcca tctatctgat caccgtggtg     120
gggaatatta gtttggtggc actgatattt acacaccgtc ggcttcacac accaatgtac     180
atctttctgg gaaatctggc tcttgtggat tcttgctgtg cctgtgctat taccccccaaa    240 atgttagaga acttcttttc tgagaacaaa aggatttccc tctatgaatg tgcagtacag     300
ttttattttc tttgcactgt ggaaactgca gactgctttc ttctggcagc aatggcctat     360
gaccgctatg tggccatatg caacccactg cagtaccaca tcatgatgtc caagaaactc     420
tgcattcaga tgaccacagg ggccttcata gctggaaacc tgcattccat gattcatgta     480
gggcttgtat ttaggttagt tttctgtgga tcgaatcaca tcaaccactt ttactgtgat     540
attcttccct tgtatagact ctcttgtgtt gatccttata tcaatgaact ggttctattc     600
atcttctcag gttcagttca agtctttacc ataggtagtg tcttaatatc ttatctctat     660
attcttctta ctattttcaa aatgaaatcc aaagagggaa gggccaaagc ttttctacc     720 tgtgcatccc actttttgtc agtttcatta ttctatggat ctcttttctt catgtacgtt     780
agaccaaatt tgcttgaaga aggggataaa gatataccag ctgcaatttt atttacaata     840
gtagttccct tactaaatcc tttcatttat agcctgagaa atagggaagt aataagtgtc     900
ttaagaaaaa ttctgatgaa gaaataa                                          927

<210> SEQ ID NO 2
<211> LENGTH: 308
<212> TYPE: PRT
<213> ORGANISM: Homo sapiens
<220> FEATURE:
<223> OTHER INFORMATION: Polypeptide of human OR5K1

<400> SEQUENCE: 2

Met Ala Glu Glu Asn His Thr Met Lys Asn Glu Phe Ile Leu Thr Gly
1               5                   10                  15

Phe Thr Asp His Pro Glu Leu Lys Thr Leu Leu Phe Val Val Phe Phe
                20                  25                  30

Ala Ile Tyr Leu Ile Thr Val Val Gly Asn Ile Ser Leu Val Ala Leu
        35                  40                  45
```

-continued

```
Ile Phe Thr His Arg Arg Leu His Thr Pro Met Tyr Ile Phe Leu Gly
    50                  55                  60

Asn Leu Ala Leu Val Asp Ser Cys Cys Ala Cys Ala Ile Thr Pro Lys
65              70              75              80

Met Leu Glu Asn Phe Phe Ser Glu Asn Lys Arg Ile Ser Leu Tyr Glu
            85              90                  95

Cys Ala Val Gln Phe Tyr Phe Leu Cys Thr Val Glu Thr Ala Asp Cys
            100             105             110

Phe Leu Leu Ala Ala Met Ala Tyr Asp Arg Tyr Val Ala Ile Cys Asn
        115             120             125

Pro Leu Gln Tyr His Ile Met Met Ser Lys Lys Leu Cys Ile Gln Met
        130             135             140

Thr Thr Gly Ala Phe Ile Ala Gly Asn Leu His Ser Met Ile His Val
145             150             155             160

Gly Leu Val Phe Arg Leu Val Phe Cys Gly Ser Asn His Ile Asn His
                165             170             175

Phe Tyr Cys Asp Ile Leu Pro Leu Tyr Arg Leu Ser Cys Val Asp Pro
            180             185             190

Tyr Ile Asn Glu Leu Val Leu Phe Ile Phe Ser Gly Ser Val Gln Val
        195             200             205

Phe Thr Ile Gly Ser Val Leu Ile Ser Tyr Leu Tyr Ile Leu Leu Thr
    210             215             220

Ile Phe Lys Met Lys Ser Lys Glu Gly Arg Ala Lys Ala Phe Ser Thr
225             230             235             240

Cys Ala Ser His Phe Leu Ser Val Ser Leu Phe Tyr Gly Ser Leu Phe
                245             250             255

Phe Met Tyr Val Arg Pro Asn Leu Leu Glu Glu Gly Asp Lys Asp Ile
            260             265             270

Pro Ala Ala Ile Leu Phe Thr Ile Val Val Pro Leu Leu Asn Pro Phe
        275             280             285

Ile Tyr Ser Leu Arg Asn Arg Glu Val Ile Ser Val Leu Arg Lys Ile
    290             295             300

Leu Met Lys Lys
305
```

INHIBITOR OF ODOR CAUSED BY FURANEOL

REFERENCE TO SEQUENCE LISTING SUBMITTED ELECTRONICALLY

The content of the electronically submitted substitute sequence listing, file name 2537_1040000_SequenceListing_ST25.txt, size 4,381 bytes; and date of creation Oct. 10, 2014, filed herewith, is incorporated herein by reference in its entirety.

FIELD OF THE INVENTION

The present invention relates to an inhibitor of an odor caused by Furaneol.

BACKGROUND OF THE INVENTION

A large number of malodorous molecules differing in polarity or molecular weight are found in our living environments. Various deodorization methods have been developed so far in order to deodorize these diverse malodorous molecules. In general, such deodorization methods are broadly classified into biological methods, chemical methods, physical methods, and sensory methods. Among the malodorous molecules, highly polar short-chain fatty acids or amines can be deodorized by the chemical method, i.e., neutralization reaction. Sulfur compounds such as thiol can be deodorized by the physical method, i.e., adsorption treatment. Still, there remain a large number of malodorous molecules which cannot be dealt with by the conventional deodorization methods. Also, the deodorization method based on adsorption treatment has a problem that it tends to cause the re-emission of a bad smell. In addition, these conventional methods may mask even odors other than the bad smell of interest. Thus, a deodorization method which can overcome these problems has been demanded.

Another known method involves deodorizing a bad smell by rendering a different odorant more strongly perceivable using a fragrance. In this method, however, the odor of the fragrance may cause discomfort. In addition, an odorous substance which exhibits an effective deodorizing effect on the malodorous substance of interest must be searched for in order to mask the bad smell by a different odorant of a perfume, a fragrance, or the like. Heretofore, sensory tests by experts have been conducted for the evaluation of odors. Such sensory tests, however, present problems such as the need of fostering experts capable of evaluating odors and low throughputs. Thus, the previous search for an odorous substance which exhibits a deodorizing effect has not been easy to achieve.

In mammals such as humans, the sense of smell works by the mechanism where odor molecules bind to olfactory receptors on olfactory nerve cells present in the olfactory epithelium in an upper portion of the nasal cavity to transmit the responses of the receptors thereto to the central nervous system. In humans, approximately 400 olfactory receptors have been reported, and genes encoding these receptors account for approximately 3% of all human genes. In general, a set of olfactory receptors is associated with a set of odor molecules. This means that individual olfactory receptors can respond to a plurality of structurally similar odor molecules with different affinities, while individual odor molecules can be recognized by a plurality of olfactory receptors. According to another report, an odor molecule activating a certain olfactory receptor functions as an antagonist inhibiting the activation of a different olfactory receptor. These combined responses of a set of olfactory receptors render individual odors perceivable.

Accordingly, when a certain odor molecule coexists with a different odor molecule, the different odor molecule may inhibit the response of a receptor corresponding to the certain odor molecule, resulting in the final perception of a different odor. Such a mechanism is called the antagonism of an olfactory receptor. The alteration of an odor caused by this receptor antagonism is a preferred deodorization approach because this approach, unlike the deodorization methods which involve adding a different odorant of a perfume, a fragrance, or the like, can specifically cancel the perception of a bad smell and does not cause discomfort derived from the odor of such a fragrance.

Skin tanning agents (also called self-tanning agents or sunless tanning agents) are skin cosmetics which colors the skin. Mainly, dihydroxyacetone (DHA) is used alone or in combination with erythrulose or the like as an ingredient which causes the skin color to turn brown. Such an ingredient reacts with the upper layer of the skin to color the skin brown. Although this coloring is believed to proceed through browning reaction, the details of a mechanism underlying this reaction have hardly been elucidated. The browning reaction is also called Maillard reaction in the field of food chemistry. This term refers to the reaction through which a nitrogen-containing compound such as an amino acid or a protein is polymerized with a reduced sugar to form a brown polymer called melanoidin. The Maillard reaction is involved in food coloring or aroma component formation caused by the heating, etc. of foods.

2,5-Dimethyl-4-hydroxy-3 (2H)-furanone (Furaneol) is a substance known to have an odor expressed as a "strong fruity caramel aroma", a "burnt caramel aroma", "burnt sugar", a "curry-like flavor", a "cotton candy smell", etc. (Non Patent Documents 1 to 4). Patent Document 1 describes a beer-tasted beverage having a taste and flavor or a fragrant smell enhanced by the formation of maltol and Furaneol in a fermentation undiluted solution.

CITATION LIST

Patent Document

[Patent Document 1] WO 2009/078360

Non Patent Document

[Non Patent Document 1] Gosei Koryo—Kagaku To Shohin Chishiki—(Synthetic Flavor and Fragrance—Chemistry and Product Knowledge—in English), 2005, The Chemical Daily Co., Ltd.
[Non Patent Document 2] J. Agric. Food Chem., 1997, 45 (6): 2217-2224
[Non Patent Document 3] ACS Symp Ser., 2002, 836: 108-123
[Non Patent Document 4] Anal Chim Acta., 2010, 657 (2): 198-203

SUMMARY OF THE INVENTION

The present invention provides an inhibitor of an odor caused by 2,5-dimethyl-4-hydroxy-3(2H)-furanone (Furaneol), comprising at least one compound selected from the group consisting of compounds described in Table 1 below as an active ingredient.

TABLE 1

ω-6-hexadecenlactone;
7-acetyl-1,2,3,4,5,6,7,8-octahydro-1,1,6,7-tetramethyl-naphthalene;
3-(4-tert-butylphenyl)propanal;
5-methyl-2-(1-methylethyl)-phenol;
oxacyclohexadecen-2-one;
(5E)-3-methylcyclopentadec-5-en-1-one;
citral;
patchouli oil;
1-(5,6,7,8-tetrahydro-3,5,5,6,8,8-hexamethyl-2-naphthalenyl)-ethanone;
4,6,6,7,8,8-hexamethyl-1,3,4,6,7,8-hexahydrocyclopenta[g]isochromene;
(E)-3-methyl-4-(2,6,6-trimethylcyclohex-2-en-1-yl)but-3-en-2-one;
muscone;
1-(2,3,4,7,8,8a-hexahydro-3,6,8,8-tetramethyl-1H-3a,7-methanoazulen-5-yl)-ethanone;
cedryl acetate;
2-ethyl-4-(2,2,3-trimethyl-3-cyclopenten-1-yl)-2-buten-1-ol;
lemon oil; and
(1-methyl-2-(1,2,2-trimethylbicyclo[3.1.0]-hex-3-ylmethyl)cyclopropyl)methanol

DETAILED DESCRIPTION OF THE INVENTION

The term "masking" in relation to odors as used herein refers to a general approach for canceling or weakening the perception of the odor of interest. The "masking" may include chemical approaches, physical approaches, biological approaches, and sensory approaches. Examples of the masking include: an arbitrary approach for removing an odor molecule causative of the odor of interest from the environment (e.g., adsorption and chemical decomposition of the odor molecule); an approach for preventing the odor of interest from being released to the environment (e.g., containment); and a method which involves adding a different odorant of a flavor, a fragrance, or the like to reduce the perception of odor of interest.

The term "masking based on olfactory receptor antagonism" as used herein refers to one form of the above-mentioned "masking" in a broad sense. This approach utilizes both of an odor molecule of the odor of interest and a different odor molecule to thereby inhibit a receptor response to the odor molecule of interest by the different odor molecule, resulting in change in odor which is perceived by individuals. The masking based on olfactory receptor antagonism is distinct from the approach of canceling the odor of interest by a different strong odorant of a fragrance or the like, even though these approaches both employ the different odor molecule. One example of the masking based on olfactory receptor antagonism is the case of using a substance, such as an antagonist, which inhibits the response of an olfactory receptor. A substance inhibiting the response of a receptor to an odor molecule responsible for a particular odor can be applied to the receptor to thereby inhibit the response of the receptor to the odor molecule. The odor which is finally perceived by individuals can therefore be changed.

The term "Furaneol" as used herein refers to 2,5-dimethyl-4-hydroxy-3(2H)-furanone. The term "odor caused by Furaneol" can be an odor brought about by 2,5-dimethyl-4-hydroxy-3(2H)-furanone. The "odor caused by Furaneol" or the "odor caused by 2,5-dimethyl-4-hydroxy-3(2H)-furanone" as used herein can be typically expressed as, for example, a caramel aroma or a burnt sugar smell. Also, the "odor caused by Furaneol" or the "odor caused by 2,5-dimethyl-4-hydroxy-3(2H)-furanone" as used herein can be an unpleasant smell generated by the application of a conventional self-tanning agent to the skin, more specifically, an unpleasant smell expressed as a "burnt sugar smell" or the like generated by the application of a skin tanning agent containing dihydroxyacetone (DHA) to the skin.

The reported problem of commercially available skin tanning agents (self-tanning agents or sunless tanning agents) is their unique unpleasant smells expressed as earthy, burnt sugar smells, etc. upon application (D. M. Hindenlang and M. E. McDonnell, Cosmetics & Toiletries magazine, 2008, Vol. 123, No. 7, p. 67-74). Thus, improvement in the smells has been demanded. As a result of examining a cause of the unpleasant smell, 2,5-dimethyl-4-hydroxy-3(2H)-furanone (Furaneol) produced via methylglyoxal from dihydroxyacetone (DHA) contained in the skin tanning agents has been found to be a causative substance. For reducing such an unpleasant smell attributed to Furaneol, it has been required to control the odor of Furaneol.

The present inventors searched for an olfactory receptor which responds to Furaneol and successfully identified the receptor. The present inventors also found that a substance inhibiting the response of the olfactory receptor can inhibit the perception of an odor caused by Furaneol by masking based on olfactory receptor antagonism.

Figure 1:
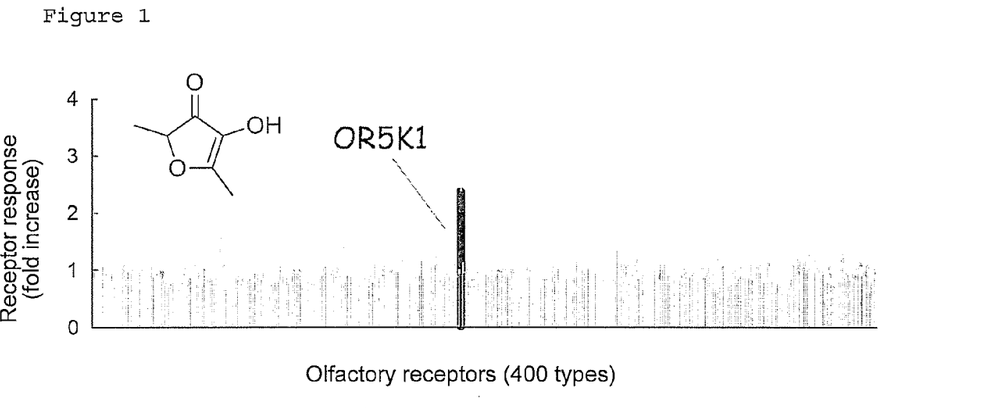
FIG. 1 shows the responses of olfactory receptors to Furaneol. The abscissa represents individual olfactory receptors. The ordinate represents response intensity.

As shown in FIG. 1, the present inventors identified an olfactory receptor OR5K1 as only one receptor responsive to Furaneol from among many olfactory receptors. OR5K1 refers to an olfactory receptor expressed on a human olfactory cell and is registered as GI: 115270955 in GenBank. OR5K1 is encoded by a gene having the nucleotide sequence represented by SEQ ID NO: 1. This protein consists of the amino acid sequence represented by SEQ ID NO: 2.

Figure 2:
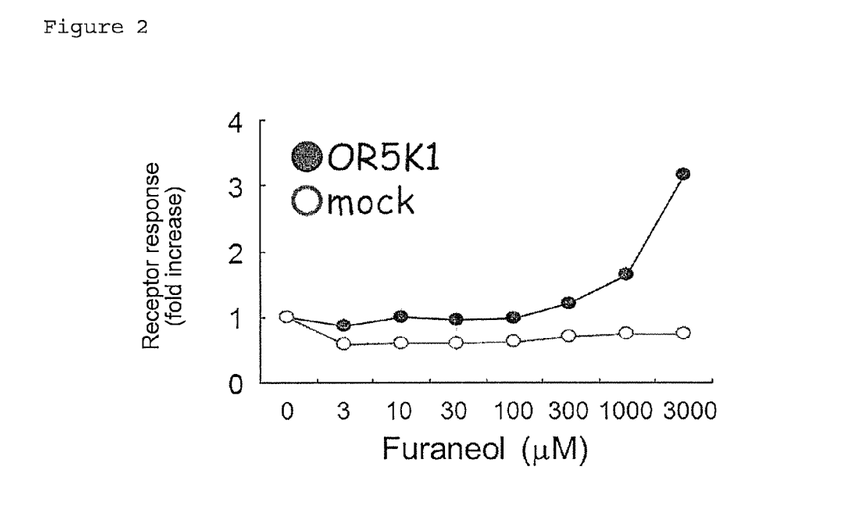
FIG. 2 shows the response of an olfactory receptor OR5K1 to varying concentrations of Furaneol. n=3, error bar=±SE.

OR5K1 is a novel receptor for Furaneol which has not been found so far to respond to Furaneol. As shown in FIG. 2, OR5K1 responds to Furaneol in a concentration-dependent manner. Thus, a substance inhibiting the response of OR5K1 can change the individual's perception of an odor caused by Furaneol in the central nervous system by masking based on olfactory receptor antagonism, resulting in the selective inhibition of the odor caused by Furaneol.

The inhibitor of an odor caused by Furaneol, provided by the present invention, can selectively deodorize the odor caused by Furaneol by masking based on olfactory receptor antagonism. Thus, the inhibitor of an odor caused by Furaneol, provided by the present invention, can deodorize the odor caused by Furaneol, for example, an unpleasant smell generated upon application of conventional self-tanning agents (also called sunless tanning agents), without causing the problems such as discomfort derived from the odor of a fragrance in conventional deodorization methods using a deodorizer or a fragrance.

Thus, according to one aspect, the present invention provides an inhibitor of an odor caused by Furaneol, comprising a substance inhibiting the response of an olfactory receptor OR5K1 as an active ingredient. The inhibitor of an odor caused by Furaneol according to the present invention functions as an antagonist of OR5K1. In other words, the inhibitor of an odor caused by Furaneol according to the present invention comprises an antagonist of OR5K1 as an active ingredient. Thus, the inhibitor of an odor caused by Furaneol according to the present invention can change the individual's perception of an odor caused by Furaneol in the central nervous system by masking based on olfactory receptor antagonism, resulting in the inhibition of the odor caused by Furaneol.

Examples of the active ingredient in the inhibitor of an odor caused by Furaneol according to the present invention include the following compounds:

ω-6-hexadecenlactone (ambrettolide);
7-acetyl-1,2,3,4,5,6,7,8-octahydro-1,1,6,7-tetramethylnaphthalene (Iso E Super);
3-(4-tert-butylphenyl)propanal (bourgeonal);
5-methyl-2-(1-methylethyl)-phenol (thymol);
oxacyclohexadecen-2-one (Habanolide®);
(5E)-3-methylcyclopentadec-5-en-1-one (Muscenone® Delta);
citral;
patchouli oil;
1-(5,6,7,8-tetrahydro-3,5,5,6,8,8-hexamethyl-2-naphthalenyl)-ethanone (Tonalid®);
4,6,6,7,8,8-hexamethyl-1,3,4,6,7,8-hexahydrocyclopenta[g]isochromene (galaxolide);
(E)-3-methyl-4-(2,6,6-trimethylcyclohex-2-en-1-yl)but-3-en-2-one (methyl ionone-G);
muscone;
1-(2,3,4,7,8,8a-hexahydro-3,6,8,8-tetramethyl-1H-3a,7-methanoazulen-5-yl)-ethanone(acetylcedrene);
cedryl acetate;
2-ethyl-4-(2,2,3-trimethyl-3-cyclopenten-1-yl)-2-buten-1-ol (bangalol);
lemon oil; and
(1-methyl-2-(1,2,2-trimethylbicyclo[3.1.0]-hex-3-ylmethyl)cyclopropyl)methanol (Javanol®).

These compounds are OR5K1 antagonists. Each of these OR5K1 antagonists can inhibit the response of the olfactory receptor OR5K1 to Furaneol by 40% or more, preferably 50% or more, more preferably 75% or more, compared with that in the absence of the antagonist. In other words, the response of the olfactory receptor OR5K1 to Furaneol in the presence of the antagonist is reduced to 60% or less, preferably 50% or less, more preferably 25% or less, of the response of the receptor in the absence of the antagonist.

Among these OR5K1 antagonists, preferred examples of the active ingredient in the inhibitor of an odor caused by Furaneol include: ω-6-hexadecenlactone (ambrettolide); 7-acetyl-1,2,3,4,5,6,7,8-octahydro-1,1,6,7-tetramethylnaphthalene (Iso E Super); 3-(4-tert-butylphenyl)propanal (bourgeonal); 5-methyl-2-(1-methylethyl)-phenol (thymol); oxacyclohexadecen-2-one (Habanolide®); (5E)-3-methylcyclopentadec-5-en-1-one (Muscenone® Delta); citral; patchouli oil; 1-(5,6,7,8-tetrahydro-3,5,5,6,8,8-hexamethyl-2-naphthalenyl)-ethanone (Tonalid®); 4,6,6,7,8,8-hexamethyl-1,3,4,6,7,8-hexahydrocyclopenta[g]isochromene (galaxolide); (E)-3-methyl-4-(2,6,6-trimethylcyclohex-2-en-1-yl)but-3-en-2-one (methyl ionone-G); muscone; and 1-(2,3,4,7,8,8a-hexahydro-3,6,8,8-tetramethyl-1H-3a,7-methanoazulen-5-yl)-ethanone (acetylcedrene).

The inhibitor of an odor caused by Furaneol according to the present invention comprises at least one compound selected from the group consisting of the OR5K1 antagonists listed above as an active ingredient. For example, the active ingredient in the inhibitor of an odor caused by Furaneol according to the present invention may be at least one compound, for example, any one compound alone or any two or more compounds in combination, selected from the group consisting of the OR5K1 antagonists listed above. Preferably, the inhibitor of an odor caused by Furaneol according to the present invention essentially consists of at least one compound selected from the group consisting of the OR5K1 antagonists.

As shown in Table 3, each of these OR5K1 antagonists inhibits the response of the olfactory receptor OR5K1 to Furaneol. These compounds have previously been known as flavor materials, but have not been known to have the function of antagonizing the response of the olfactory receptor to Furaneol to selectively inhibit the odor caused by Furaneol.

A commercially available product can be purchased as any of the OR5K1 antagonists listed above (see Motoichi Indo, "Gosei Koryo—Kagaku To Shohin Chishiki—(Synthetic Flavors—Chemistry and Product Knowledge—in English)", enlarged and revised edition, The Chemical Daily Co., Ltd., issued in March 2005). These antagonists are available from, for example, Firmenich S. A., Givaudan S. A., International Flavors & Fragrances Inc., Takasago International Corp., and Kao Corp.

According to another aspect of the present invention, the OR5K1 antagonists listed above can each be used as an active ingredient for inhibiting an odor caused by Furaneol, for example, a caramel aroma, a burnt sugar smell, or an unpleasant smell (e.g., a burnt sugar smell) generated by the application of a self-tanning agent to the skin or upon application of a product containing dihydroxyacetone (DHA).

In one embodiment, the OR5K1 antagonists listed above can each be contained as an active ingredient for inhibiting an odor caused by Furaneol in a compound or a composition for inhibiting an odor caused by Furaneol. Alternatively, the OR5K1 antagonists listed above can each be used for production of an inhibitor of an odor caused by Furaneol or for production of a compound or a composition for inhibiting an odor caused by Furaneol.

In one embodiment, the OR5K1 antagonists listed above can each be used as an active ingredient for inhibiting an odor caused by Furaneol in every compound or composition desired to inhibit an odor caused by Furaneol or in every environment desired to inhibit an odor caused by Furaneol. Alternatively, the OR5K1 antagonists can each be used as an active ingredient for inhibiting an odor caused by Furaneol, for production of a compound or a composition desired to inhibit an odor caused by Furaneol. Examples of the compound or the composition desired to inhibit an odor caused by Furaneol include skin tanning agents (also called self-tanning agents or sunless tanning agents), for example, a skin tanning agent containing dihydroxyacetone (DHA) as a coloring agent and other skin tanning agents which employ browning reaction, and other products containing DHA. Furaneol excessively contained in a food or a drink may work as an off-flavor. For example, the presence of excessive Furaneol in powdered milk reduces its taste and flavor. Thus, other examples of the compound or the composition desired to inhibit an odor caused by Furaneol include foods or drinks desired to reduce the odor of Furaneol and compositions containing the foods or the drinks.

The inhibitor of an odor caused by Furaneol, and the compound or the composition for inhibiting an odor caused by Furaneol may appropriately contain an additional ingredient having a deodorizing effect according to the purpose, in addition to any of the OR5K1 antagonists listed above. Any of generally known deodorizers having a chemical. or physical deodorizing effect can be used as the additional ingredient having a deodorizing effect. Examples thereof include deodorizing active ingredients extracted from plants (e.g., green tea extracts), organic acids, various amino acids and their salts, glyoxal, oxidants, flavonoids, catechins, polyphenols, porous substances (e.g., active carbon and zeolite), inclusion compounds (e.g., cyclodextrins), photocatalysts, and various masking agents. The inhibitor, and the compound or the composition for inhibiting an odor caused by Furaneol may further comprise an optional ingredient which is generally added to a deodorizer or a smell-preventing agent.

According to a further aspect, the present invention provides a method for inhibiting an odor caused by Furaneol, comprising the step of allowing any of the OR5K1 antagonists listed above to coexist with the odor caused by Furaneol.

In one embodiment, this method involves applying at least one compound selected from the group consisting of the OR5K1 antagonists listed above to an individual to allow the antagonist to coexist with the odor caused by Furaneol, wherein the individual is in need of inhibition of the perception of the odor caused by Furaneol in the presence of the odor, preferably in need of inhibition of the perception of the odor caused by Furaneol by masking based on olfactory receptor antagonism. As a result, the antagonist binds to OR5K1 to inhibit the response of OR5K1 to Furaneol. Masking based on olfactory receptor antagonism therefore takes place to thereby inhibit the odor caused by Furaneol. In the method, preferred examples of the OR5K1 antagonist are the same as those mentioned above in relation to the inhibitor of an odor caused by Furaneol.

In the method of the present invention, the individual can be any mammal without particular limitations and is preferably a human. More specifically, examples of the individual in need of inhibition of the perception of the odor caused by Furaneol in the method of the present invention include humans who use skin tanning agents (also called self-tanning agents or sunless tanning agents), more specifically, a skin tanning agent containing dihydroxyacetone (DHA) as a coloring agent or other skin tanning agents which employ browning reaction, humans who use other products containing DHA, and humans who desire reduction in the odor caused by Furaneol from foods or drinks, for example, humans who take a food or a drink, such as powdered milk, in which the presence of excessive Furaneol reduces its taste and flavor.

In one embodiment of the method of the present invention, the OR5K1 antagonist is added to a compound or a composition containing Furaneol. This reduces the response of the olfactory receptor to Furaneol contained in the compound or the composition and inhibits the individual's perception of the odor caused by Furaneol, resulting in the inhibition of the odor caused by Furaneol. In another embodiment, the OR5K1 antagonist is added to a compound or a composition which may produce Furaneol. This reduces the response of the olfactory receptor to Furaneol produced from the compound or the composition and inhibits the individual's perception of the odor caused by Furaneol, resulting in the inhibition of the odor caused by Furaneol. Examples of the compound or the composition which may produce Furaneol include skin tanning agents, for example, a skin tanning agent containing dihydroxyacetone (DHA) as a coloring agent and other skin tanning agents which employ browning reaction, and other products containing DHA.

The following composition, production method, use, or method will be further disclosed herein as an exemplary embodiment of the present invention. However, the present invention is not intended to be limited by these embodiments.

<1> An inhibitor of an odor caused by Furaneol, comprising at least one compound selected from the group consisting of the compounds described in Table 1 as an active ingredient.

<2> Use of at least one compound selected from the group consisting of the compounds described in Table 1 for inhibition of an odor caused by Furaneol.

<3> Use of at least one compound selected from the group consisting of the compounds described in Table 1 for production of an inhibitor of an odor caused by Furaneol.

<4> At least one compound selected from the group consisting of the compounds described in Table 1 for use in the inhibition of an odor caused by Furaneol.

<5> A method for inhibiting an odor caused by Furaneol, comprising allowing at least one compound selected from the group consisting of the compounds described in Table 1 to coexist with the odor caused by Furaneol.

<6> The inhibitor, the use, the compound, or the method according to any of <1> to <5>, wherein the at least one compound selected from the group consisting of the compounds described in Table 1 is preferably at least one compound selected from the group consisting of the following compounds:

ω-6-hexadecenlactone; 7-acetyl-1,2,3,4,5,6,7,8-octahydro-1,1,6,7-tetramethyl-naphthalene; 3-(4-tert-butylphenyl)propanal; 5-methyl-2-(1-methylethyl)-phenol; oxacyclohexadecen-2-one; (5E)-3-methylcyclopentadec-5-en-1-one; citral; patchouli oil; 1-(5,6,7,8-tetrahydro-3,5,5,6,8,8-hexamethyl-2-naphthalenyl)-ethanone; 4,6,6,7,8,8-hexamethyl-1,3,4,6,7,8-hexahydrocyclopenta[g]isochromene; (E)-3-methyl-4-(2,6,6-trimethylcyclohex-2-en-1-yl)but-3-en-2-one; muscone; and 1-(2,3,4,7,8,8a-hexahydro-3,6,8,8-tetramethyl-1H-3a,7-methanoazulen-5-yl)-ethanone.

EXAMPLES

Hereinafter, the present invention will be described more specifically with reference to Examples.

Example 1 Identification of Olfactory Receptor Responding to Furaneol

1) Cloning of Human Olfactory Receptor Gene

On the basis of sequence information registered in GenBank, each human olfactory receptor gene was cloned by PCR with Human Genomic DNA Female (G1521: Promega Corp.) as a template. Each gene thus amplified by PCR was inserted into a pENTR vector (Invitrogen Corp.) according to the manual. A NotI-AscI site present on the pENTR vector was recombined into a NotI-AscI site prepared downstream of a Flag-Rho tag sequence on a pME18S vector.

2) Preparation of pME18S-Human RTP1S Vector

A gene (GenBank GI: 50234917) encoding a human receptor transporting protein, RTP1S was inserted into the EcoRI-XhoI site of the pME18S vector.

3) Preparation of Olfactory Receptor-Expressing Cell

HEK293 cells expressing each of 400 types of human olfactory receptors were prepared. Each reaction solution having the composition shown in Table 2 was prepared, then left standing for 15 minutes in a clean bench, and then added to each well of a 96-well plate (Becton, Dickinson and Company). Subsequently, the HEK293 cells ($3\times10^5$ cells/$cm^2$) were inoculated thereto at 100 μL/well and then cultured at 37° C. for 24 hours in an incubator kept at 5% $CO_2$.

TABLE 2

| | |
|---|---|
| OPTI-MEM (GIBCO) | 50 μL |
| Human olfactory receptor gene (inserted to N-terminally Flag-Rho-tagged pME18S vector) | 0.075 μg |
| pGL4.29 (fluc2P-CRE-hygro, Promega) | 0.03 μg |
| pGL4.75 (hRluc-CMV, Promega) | 0.03 μg |
| pME18S-human RTP1S vector | 0.03 μg |
| lipofectamine 2000 (Invitrogen) | 0.4 μL |

4) Luciferase Assay

The olfactory receptors expressed on the HEK293 cells are conjugated with intracellular Gαs to activate adenylate cyclase, thereby increasing intracellular cAMP levels. In this study, their responses to Furaneol were measured using luciferase reporter gene assay which involved monitoring increase in intracellular cAMP level as luminescence intensity derived from a firefly luciferase gene (fluc2P-CRE-hygro). In addition, the cells were cotransfected with the reporter gene and a fusion gene (hRluc-CMV) of a *Renilla* luciferase gene downstream of a CMV promoter for use as an internal standard for correcting transfection efficiency or an error in the number of cells.

A medium was removed from the cultures prepared in the preceding paragraph 3). To the resulting cultures, 75 μL of a solution containing Furaneol (3 mM) prepared with a CD293 medium (Invitrogen Corp.) was added. The cells were cultured for 2.5 hours in a $CO_2$ incubator to express the luciferase genes at sufficient levels in the cells. The luciferase activity was measured using Dual-Glo™ luciferase assay system (Promega Corp.) according to the instruction manual of the product. Firefly luciferase-derived luminescence intensity induced by stimulation with Furaneol was divided by luminescence intensity in the cells without Furaneol stimulation to calculate a value as fold increase, which was in turn used as an index for response intensity.

5) Results

As a result of measuring the responses of 400 types of olfactory receptors to Furaneol (3 mM), only the olfactory receptor OR5K1 exhibited a response to Furaneol (FIG. 1). OR5K1 is a novel Furaneol receptor which has not been found so far to respond to Furaneol.

Example 2 Concentration-Dependent Response of OR5K1 to Furaneol

The olfactory receptor OR5K1 (GenBank GI: 115270955, SEQ ID NO: 2) was expressed, together with human RTP1S, on HEK293 cells by the same procedures as in Example 1 and then examined for the concentration dependence of its response to varying concentrations of Furaneol (0, 3, 10, 30, 100, 300, 1000, and 3000 μM). As a result, OR5K1 exhibited a concentration-dependent response to Furaneol (FIG. 2).

Example 3 Identification of OR5K1 Antagonist 84 types of test substances were examined for their antagonistic activity against the response of the olfactory receptor OR5K1 to Furaneol.

Furaneol (3 mM) and each test substance (100 μM) were added to HEK293 cells allowed to express the olfactory receptor OR5K1 by the same procedures as in Example 2. The response of the olfactory receptor was measured to evaluate change in receptor response caused by the addition of the test substance.

The rate of inhibition of the receptor response by the test substance was calculated as follows: firefly luciferase-derived luminescence intensity (Y) in the olfactory receptor OR5K1-expressing cells without Furaneol stimulation was subtracted from luminescence intensity (X) induced by stimulation with Furaneol alone to determine receptor activity (X−Y) based on the stimulation with Furaneol alone. Likewise, the luminescence intensity (Y) in the cells without Furaneol stimulation was subtracted from luminescence intensity (Z) induced by stimulation with the mixture of Furaneol and the test substance to determine receptor activity (Z−Y) in the presence of the test substance. The rate of reduction in the receptor activity (Z−Y) in the presence of the test substance with respect to the receptor activity (X−Y) based on the stimulation with Furaneol alone was calculated according to an expression shown below to determine the rate of inhibition of the receptor response by the test substance. In this assay, a plurality of independent duplicate experiments were performed. An average of the experiments in each run was obtained.

Rate of inhibition (%)={1−(Z−Y)/(X−Y)}×100

As a result, 17 types of test substances had 40% or higher rate of inhibition of the response of OR5K1 to Furaneol (reduced the response to 60% or less), demonstrating that these test substances have antagonistic activity against OR5K1 (Table 3).

TABLE 3

| | |
|---|---|
| 75% or more rate of inhibition (response was reduced to 25% or less; very strong antagonist) | ω-6-Hexadecenlactone (ambrettolide)<br>7-Acetyl-1,2,3,4,5,6,7,8-octahydro-1,1,6,7-tetramethyl-naphthalene (Iso E Super)<br>3-(4-tert-Butylphenyl)propanal (bourgeonal)<br>5-Methyl-2-(1-methylethyl)-phenol (thymol)<br>Oxacyclohexadecen-2-one (Habanolide(R))<br>(5E)-3-Methylcyclopentadec-5-en-1-one (Muscenone(R) Delta)<br>Citral<br>Patchouli oil<br>1-(5,6,7,8-tetrahydro-3,5,5,6,8,8-hexamethyl-2-naphthalenyl)-ethanone (Tonalid(R))<br>4,6,6,7,8,8-Hexamethyl-1,3,4,6,7,8-hexahydrocyclopenta[g]isochromene (galaxolide)<br>(E)-3-Methyl-4-(2,6,6-trimethylcyclohex-2-en-1-yl)but-3-en-2-one (methyl ionone-G)<br>Muscone<br>1-(2,3,4,7,8,8a-hexahydro-3,6,8,8-tetramethyl-1H-3a,7-methanoazulen-5-yl)-ethanone (acetylcedrene) |
| 50% or more rate of inhibition (response was reduced to 50% or less; strong antagonist) | Cedryl acetate<br>2-Ethyl-4-(2,2,3-trimethyl-3-cyclopenten-1-yl)-2-buten-1-ol (bangalol) |
| 40% or more rate of inhibition (response was | Lemon oil<br>(1-Methyl-2-(1,2,2-trimethylbicyclo[3.1.0]-hex-3-ylmethyl)cyclopropyl)methanol |

TABLE 3-continued

| | |
|---|---|
| reduced to 60% or less; weak antagonist) | (Javanol(R)) |

Example 4 Evaluation on Ability of OR5K1 Antagonist to Inhibit Odor of Furaneol Each test substance having antagonistic activity against OR5K1, identified in Example 3, was confirmed by a sensory test for its ability to inhibit the odor of Furaneol. Each panelist smelled 0.5 g of Furaneol (1%)-containing cloth supplemented with 0.5 µL of a flavor, and then evaluated the intensity of the odor of Furaneol compared with cloth non-supplemented with the flavor. The sensory evaluation test was conducted by 3 panelists. The odor of Furaneol was evaluated as 1 when strongly perceivable and as 5 when not perceivable.

Figure 3:
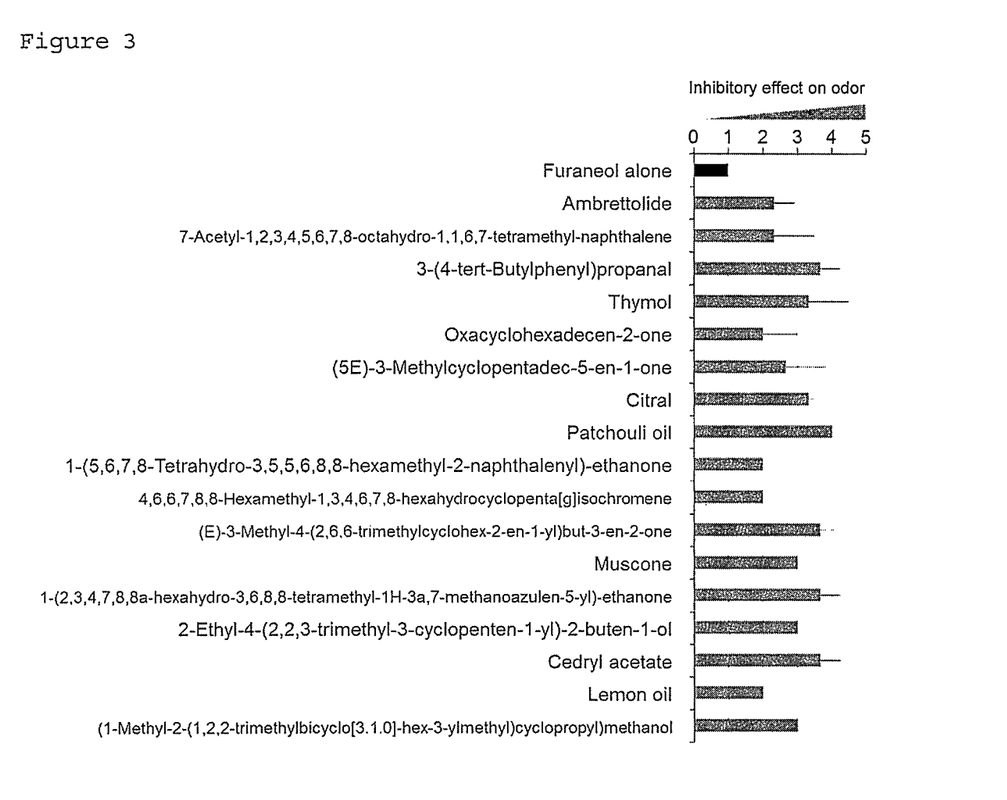
FIG. 3 shows results of sensory evaluation on the inhibitory effects of various compounds on the odor of Furaneol. error bar=±SE.

As a result, all the 17 types of test substances demonstrated to inhibit the response of OR5K1 to Furaneol in Example 3 inhibited the odor of Furaneol (FIG. 3).

The invention claimed is:

1. A method for masking an individual's perception of an odor caused by 2,5-dimethyl-4-hydroxy-3(2H)-furanone, comprising
(a) allowing at least one compound selected from the group consisting of the following compounds:
3-(4-tert-butylphenyl)propanal;
7-acetyl-1,2,3,4,5,6,7,8-octahydro-1,1,6,7-tetramethylnaphthalene;
5-methyl-2-(1-methylethyl)-phenol;
(5 E)-3-methylcyclopentadec-5-en-1-one;
patchouli oil;
1-(5,6,7,8-tetrahydro-3,5,5,6,8,8-hexamethyl-2-naphthalenyl)-ethanone;
muscone;
1-(2,3,4,7,8,8a-hexahydro-3,6,8,8-tetramethyl-1H-3a,7-methanoazulen-5-yl)-ethanone;
cedryl acetate;
and
(1-methyl-2-(1,2,2-trimethylbicyclo[3.1.0]-hex-ylmethyl)cyclopropyl)methanol;

to coexist with the odor caused by 2,5-dimethyl-4-hydroxy-3(2H)-furanone by:
(i) applying the at least one compound to an individual in need of inhibition of the perception of the odor caused by 2,5-dimethyl-4-hydroxy-3 (2H)-furanone;
(ii) applying, to an individual in need of the perception of the odor caused by 2,5-dimethyl-4-hydroxy-3(2H)-furanone, a composition that comprises the at least one compound and the 2,5-dimethyl-4-hydroxy-3 (2H)-furanone; or
(iii) applying, to an individual in need of the perception of the odor caused by 2,5-dimethyl-4-hydroxy-3(2H)-furanone, a composition that comprises the at least one compound and that produces 2,5-dimethyl-4-hydroxy-3(2H)-furanone; and
(b) inhibiting the individual's olfactory receptor response to the 2,5-dimethyl-4-hydroxy-3(2H)-furanone by olfactory receptor antagonism of the individual's OR5K1 olfactory receptor with the at least one compound, thus masking the individual's perception of the odor caused by the 2,5-dimethyl-4-hydroxy-3 (2H)-furanone.

2. The method according to claim 1, wherein to allow the at least one compound to coexist with the odor caused by 2,5-dimethyl-4-hydroxy-3(2H)-furanone is (i) applying the at least one compound to an individual in need of inhibition of the perception of the odor caused by 2,5-dimethyl-4-hydroxy-3(2H)-furanone.

3. The method according to claim 1, wherein to allow the at least one compound to coexist with the odor caused by 2,5-dimethyl-4-hydroxy-3(2H)-furanone is (ii) applying, to the individual in need, a composition that comprises the at least one compound and the 2,5-dimethyl-4-hydroxy-3(2H)-furanone.

4. The method according to claim 1, wherein to allow the at least one compound to coexist with the odor caused by 2,5-dimethyl-4-hydroxy-3(2H)-furanone is (iii) applying, to the individual in need, a composition that comprises the at least one compound and that produces 2,5-dimethyl-4-hydroxy-3(2H)-furanone.

5. The method according to claim 1, wherein the individual is a human.

6. The method according to claim 1, wherein the odor caused by 2,5-dimethyl-4-hydroxy-3(2H)-furanone is from a skin tanning agent.

7. The method according to claim 1, wherein the odor caused by 2,5-dimethyl-4-hydroxy-3(2H)-furanone is from a food or drink.

8. The method according to claim 1, wherein the at least one compound comprises 3-(4-tert-butylphenyl)propanal.

9. The method according to claim 1, wherein the at least one compound comprises 7-acetyl-1,2,3,4,5,6,7,8-octahydro-1,1,6,7-tetramethyl-naphthalene.

10. The method according to claim 1, wherein the at least one compound comprises 5-methyl-2-(1-methylethyl)-phenol.

11. The method according to claim 1, wherein the at least one compound comprises (5E)-3-methylcyclopentadec-5-en-1-one.

12. The method according to claim 1, wherein the at least one compound comprises patchouli oil.

13. The method according to claim 1, wherein the at least one compound comprises 1-(5,6,7,8-tetrahydro-3,5,5,6,8,8-hexamethyl-2-naphthalenyl)-ethanone.

14. The method according to claim 1, wherein the at least one compound comprises muscone.

15. The method according to claim 1, wherein the at least one compound comprises 1-(2,3,4,7,8,8a-hexahydro-3,6,8,8-tetramethyl-1H-3a,7-methanoazulen-5-yl)-ethanone.

16. The method according to claim 1, wherein the at least one compound comprises cedryl acetate.

17. The method according to claim 1, wherein the at least one compound comprises (1-methyl-2-(1,2,2-trimethylbicyclo[3.1.0]-hex-3-ylmethyl)cyclopropyl)methanol.

18. The method of claim 2, wherein the applying is in the presence of the odor caused by 2,5-dimethyl-4-hydroxy-3(2H)-furanone.

* * * * *